(12) United States Patent
Okada

(10) Patent No.: US 9,277,959 B2
(45) Date of Patent: Mar. 8, 2016

(54) MEDICAL TREATMENT INSTRUMENT

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 75 days.

(21) Appl. No.: 14/211,857

(22) Filed: Mar. 14, 2014

(65) Prior Publication Data

US 2014/0288555 A1     Sep. 25, 2014

Related U.S. Application Data

(63) Continuation of application No. PCT/JP2013/071045, filed on Aug. 2, 2013.

(30) Foreign Application Priority Data

Aug. 13, 2012 (JP) ................................. 2012-179509

(51) Int. Cl.
*A61B 18/14* (2006.01)
*A61B 18/00* (2006.01)
(Continued)

(52) U.S. Cl.
CPC .............. *A61B 18/14* (2013.01); *A61B 18/1492* (2013.01); *A61B 2017/00269* (2013.01);
(Continued)

(58) Field of Classification Search
CPC ............... A61B 18/14; A61B 18/1492; A61B 2018/1475; A61B 2018/1422; A61B 2017/291; A61B 2017/2911; A61B 2017/00269; A61B 2017/00424; A61B 2017/2937; A61B 2017/2946
See application file for complete search history.

(56) References Cited

U.S. PATENT DOCUMENTS 3,903,892 A * 9/1975 Komiya ................. 606/110
4,043,323 A * 8/1977 Komiya ................. 600/104
(Continued)

FOREIGN PATENT DOCUMENTS

JP     A-62-64355      3/1987
JP     U-1-77703       5/1989
(Continued)

OTHER PUBLICATIONS

Office Action issued in Japanese Patent Application No. 2014-510598 dated May 13, 2014 (with translation).
(Continued)

*Primary Examiner* — Michael Peffley
(74) *Attorney, Agent, or Firm* — Oliff PLC

(57) ABSTRACT

A medical treatment instrument operation unit includes a sliding portion capable of advancing and retracting to a body portion and rotating around a longitudinal axis of the body portion and connected to a proximal end portion of the operating member, and a regulating portion switchable to a movable state where regulating portion is capable of advancing, retracting, and rotating to the body portion and a limited state where the advance, retraction, and rotation of sliding portion to the body portion is limited. The regulating portion includes a rotatable dial portion, and a shaft-shaped member screwed to the dial portion to be relatively advanceable and retractable thereto in a direction in which the shaft-shaped member is brought close to and separated from the body portion. Movable and limited states are switched as the shaft-shaped member comes close to and separates from the body portion with the turning of the dial portion.

8 Claims, 11 Drawing Sheets

(51) Int. Cl.
   *A61B 17/00* (2006.01)
   *A61B 17/29* (2006.01)
(52) U.S. Cl.
   CPC ......... *A61B2017/00424* (2013.01); *A61B 2017/2911* (2013.01); *A61B 2017/2937* (2013.01); *A61B 2017/2946* (2013.01); *A61B 2018/0091* (2013.01); *A61B 2018/1422* (2013.01); *A61B 2018/1475* (2013.01)

(56) References Cited

U.S. PATENT DOCUMENTS

| | | | | |
|---|---|---|---|---|
| 4,467,802 | A | * | 8/1984 | Maslanka ............... 606/206 |
| 4,718,419 | A | | 1/1988 | Okada |
| 5,766,184 | A | * | 6/1998 | Matsuno et al. ......... 606/142 |
| 6,162,209 | A | * | 12/2000 | Gobron et al. ........... 606/1 |
| 6,210,398 | B1 | | 4/2001 | Ouchi |
| 8,052,681 | B2 | * | 11/2011 | Sugita ..................... 606/45 |
| 2008/0091196 | A1 | | 4/2008 | Deal |
| 2008/0306334 | A1 | | 12/2008 | Okada |

FOREIGN PATENT DOCUMENTS

| | | |
|---|---|---|
| JP | A-11-332870 | 12/1999 |
| JP | A-2001-37765 | 2/2001 |
| JP | B2-3923022 | 5/2007 |
| JP | A-2008-302216 | 12/2008 |

OTHER PUBLICATIONS

International Search Report issued in International Patent Application No. PCT/JP2013/071045 dated Aug. 27, 2013 (with translation).

* cited by examiner

MEDICAL TREATMENT INSTRUMENT

This application is a continuation claiming priority on the basis of Japanese Patent Application No. 2012-179509 filed in Japan on Aug. 13, 2012 and based on PCT/JP2013/071045 filed on Aug. 2, 2013. The contents of both the Japanese Patent Application and the PCT Application are incorporated herein by reference.

The present invention relates to a medical treatment instrument.

BACKGROUND OF THE INVENTION

1. Field of the Invention

The present invention relates to a medical treatment instrument.

2. Description of Related Art

In the related art, medical treatment tools for performing various kinds of treatment on a living body tissue have been studied.

For example, a high-frequency knife described in Japanese Patent No. 3923022 includes a sheath, and an operation unit provided at a base end of the sheath. A tubular stopper member is coupled to a tip of the sheath. A conductive operating wire (operating member) is inserted through the inside of the sheath so as to be movable in an axis direction. A distal end portion of the operating wire is mounted with a stopper receiving portion that abuts against the aforementioned stopper member. A knife unit (treatment unit) is connected to the stopper receiving portion. A tip of the knife unit is formed with a bent portion that is substantially bent at a right angle.

The operation unit includes a substantially shaft-shaped operation unit body (body portion), and an operating slider (sliding portion) that is slidable in an axis direction with respect to the operation unit body. A rotor provided at a base end of the sheath is rotatably connected to the operation unit body.

The operating wire can be advanced and retracted in the axis direction in an inner hole of the sheath by the sliding operation of the operating slider in the axis direction, and the knife unit can be protruded and retracted from the distal end portion of the sheath by the advance/retraction operation of the operating wire. The rotation of the knife unit can be suppressed by the contact pressure generated when the stopper receiving portion contacts to the stopper member.

When it is desired to change the orientation of the bent portion around the axis during treatment, the operating slider is slightly moved rearward (pulled back) with respect to the operation unit body, and the stopper receiving portion is separated from the stopper member. If the sheath is gripped and the operation unit is rotated around the axis, the knife unit rotates simultaneously around the axis, and the orientation of the bent portion changes. When the bent portion has the desired orientation, the operating slider is moved forward (pushed) with respect to the operation unit body, and the stopper receiving portion is pressed against the stopper member. At this time, even if an external force is applied to the knife unit, the orientation of the bent portion is not changed by the aforementioned contact pressure.

However, in the high-frequency knife, a state where the stopper receiving portion is pressed against the stopper member, that is, the operating slider is pushed, should be maintained in order for the orientation of the knife unit not to change.

A high-frequency knife is described also in the specification of United States Patent Application, Publication No. 2008-0306334. The high-frequency knife described in the specification of United States Patent Application, Publication No. 2008-0306334 is different from the high-frequency knife described in the aforementioned Japanese Patent No. 3923022 in that a linear member inserted through the sheath has a structure in which an energizing wire is inserted into a coiled sheath, and a ratchet mechanism is provided.

The coiled sheath is a member having higher rigidity when being compressed.

The aforementioned ratchet mechanism is provided at the operation unit, and limits pull-back of the operating slider. The ratchet mechanism has a plurality of teeth provided at the operation unit body closer to a tip side than the operating slider, and a claw pivoted at the tip of the operating slider by a pin and biased by a spring in a direction in which the claw meshes with the teeth. When the ratchet mechanism is released to pull back the operating slider, the engagement between the claw and the teeth is released by pushing a button at a base end of the claw so as to be brought close to the axis of the sheath.

In the high-frequency knife configured in this way, if the operating slider is pushed with respect to the operation unit body, the linear member is compressed and the coiled sheath becomes rigid. Since the ratchet mechanism is provided, it is not necessary to continue holding the operating slider in order to maintain the compressed state of the linear member, and the operating slider can be released from the hand. When the knife unit is made to protrude from the tip of the sheath, is moved, and performs incision, the coiled sheath becomes rigid, deflection can be prevented, and a sufficient amount of incision with respect to a traveling distance can be performed.

SUMMARY OF THE INVENTION

A medical treatment instrument of a first aspect of the present invention includes a sheath; an operating member which is advanced and retracted, and inserted into the sheath; a treatment unit which is provided at a distal end portion of the operating member; and an operation unit which has a body portion connected to a proximal end portion of the sheath and which causes the operating member to be advanced and retracted with respect to the sheath and to be rotated around a longitudinal axis of the body portion. The operation unit includes a sliding portion which is provided so as to be capable of advancing and retracting with respect to the body portion and rotating around the longitudinal axis of the body portion and which is connected to a proximal end portion of the operating member; and a regulating portion which is switchable to a movable state where the regulating portion is capable of advancing, retracting, and rotating with respect to the body portion and a limited state where the advance, retraction, and rotation of the sliding portion with respect to the body portion is limited. The regulating portion includes a dial portion which is rotatable around an axis orthogonal to the longitudinal axis; and a shaft-shaped member which is screwed to the dial portion and is capable of advancing and retracting relative to the dial portion in a direction in which the shaft-shaped member comes close to and separates from the body portion. The movable state and the limited state are switched as the shaft-shaped member comes close to and separates from the body portion with the turning of the dial portion.

According to a second aspect of the present invention based on the above first aspect, the body portion may have a body-side finger-hooking portion, the sliding portion may have a sliding-side finger-hooking portion located further toward a tip side than the body-side finger-hooking portion, and the regulating portion may be provided further toward the tip side than the sliding-side finger-hooking portion.

According to a third aspect of the present invention based on the above second aspect, at least a portion of the dial portion may be exposed to an outside from an outer peripheral surface of the sliding portion.

According to a fourth aspect of the present invention based on the above third aspect, a hole that penetrates in a direction of the axis of the dial portion may be formed in one of the dial portion and the shaft-shaped member. A female thread may be formed in an inner peripheral surface of the hole. The shaft-shaped member may advance and retract in the direction of the axis with respect to the dial portion in response to the turning of the dial portion by a male thread to be screwed to the female thread being formed in an outer peripheral surface of the other of the dial portion and the shaft-shaped member.

According to a fifth aspect of the present invention based on the above third aspect, a plane parallel to an advance and retraction direction of the sliding portion for contacting to an end portion of the shaft-shaped member may be formed on the shaft-shaped member side of the body portion.

According to a sixth aspect of the present invention based on the above fourth aspect, the end portion of the body portion side of the shaft-shaped member may be provided with an elastic member that contact to the plane.

DETAILED DESCRIPTION OF THE INVENTION

First Embodiment

Hereinafter, a first embodiment of a medical treatment instrument related to the present invention will be described referring to FIGS. 1 to 13, taking a case where the medical treatment instrument is a high-frequency knife as an example.

Figure 1:
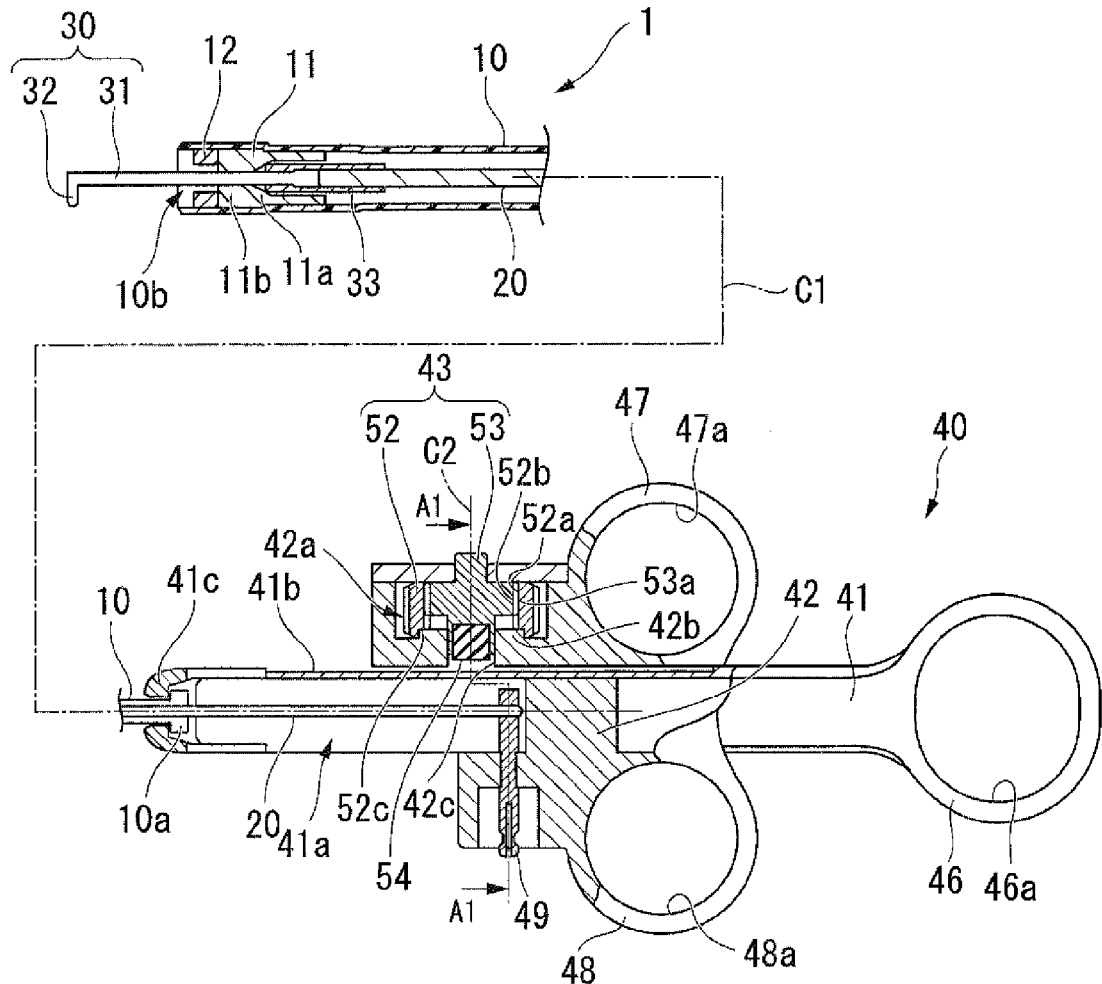
FIG. 1 is a cross-sectional view of a side surface when a high-frequency knife of a first embodiment of the present invention is brought into a push state and a movable state.
Figure 2:
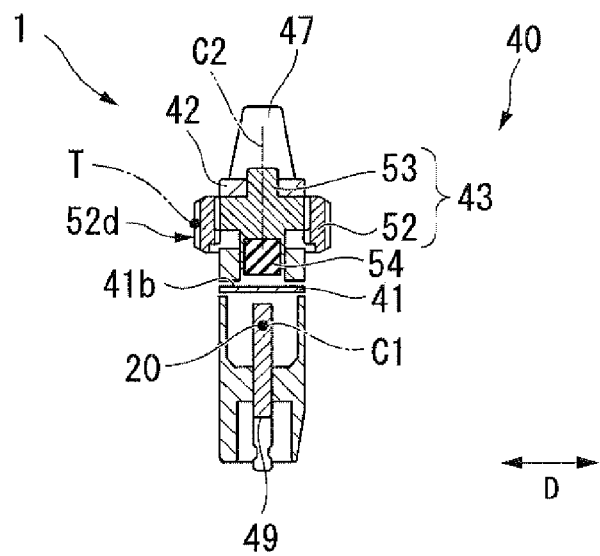
FIG. 2 is a cross-sectional view of cutting line A1-A1 in FIG. 1.

As shown in FIGS. 1 and 2, a high-frequency knife 1 of the present embodiment includes a sheath 10 having flexibility such that the sheath is insertable through a channel of an endoscope (not shown), an operating wire (operating member) 20 retractably inserted through the sheath 10, a knife unit (treatment unit) 30 provided at a distal end portion of the operating wire 20, and an operation unit 40 provided at a proximal end portion of the sheath 10.

The sheath 10 is formed in a tubular shape, and a proximal end portion of the sheath 10 is provided with a rotor 10a configured to have a larger diameter than that on a tip side. The sheath 10 is formed from a material having insulation, such as a tetrafluoroethylene material. A distal end portion of the sheath 10 is provided with a tubular stopper member 11, and an outer periphery of the stopper member 11 is covered with the distal end portion of the sheath 10. A tapered portion 11a configured to have a smaller internal diameter towards the tip side, and a smaller-diameter hole 11b located on the tip side of the tapered portion 11a is formed in an inner surface of the stopper member 11.

A ring-shaped sheath-tip insulating tip 12 that centers the knife unit 30 is disposed further toward the tip side than the stopper member 11. An outer peripheral side of the sheath-tip insulating tip 12 is covered with the sheath 10. The distal end portion of the sheath 10 is provided to extend to the tip side over the distal end portion of the sheath-tip insulating tip 12. An accommodating portion 10b, which is an internal space of the distal end portion of the sheath 10 and accommodates a bent portion 32 of the knife unit 30 to be described below, is formed further toward the tip side than the sheath-tip insulating tip 12.

The knife unit 30 has a rod-shaped electrode portion 31 arranged on an axis C1 of the sheath 10, and a bent portion 32 that is provided at a distal end portion of the electrode portion 31 and extends in a direction substantially orthogonal to the axis C1.

The external diameter of the electrode portion 31 is set so that the electrode portion 31 is insertable through the smaller-diameter hole 11b of the stopper member 11 and a conduit line of the sheath-tip insulating tip 12. The electrode portion 31 and the bent portion 32 are integrally formed from a conductive material, such as metal.

A proximal end portion of the electrode portion 31 and a distal end portion of the operating wire 20 are connected together by a stopper receiving portion 33 formed in a tubular shape from a conductive material. The external diameter of the stopper receiving portion 33 is set to be greater than the internal diameter of the smaller-diameter hole 11b of the stopper member 11, and when the stopper receiving portion 33 moves to the tip side, the stopper receiving portion 33 abuts against the stopper member 11.

The operation unit 40 has a body portion 41 provided at the proximal end portion of the sheath 10, a sliding portion 42 made movable in a direction of the axis C1 with respect to the body portion 41, and a regulating portion 43 that limits that the sliding portion 42 moves in the direction of the axis C1 with respect to the body portion 41.

In the present embodiment, the body portion 41 is formed in the shape of a rod that extends in the direction of the axis C1.

A guide groove 41a is formed along the axis C1 in the body portion 41, and a body-side finger-hooking portion 46 is provided at the proximal end portion. A body-side through-hole 46a that is formed on the axis C1 and penetrates in an orthogonal direction D orthogonal to the axis C1 (refer to FIG. 2) is formed in the body-side finger-hooking portion 46. The size of the body-side through-hole 46a is set to a size such that the thumb of an operator, such as a surgeon, is insertable the through-hole.

A planar portion (plane) 41b parallel to an axis C1 is formed in an outer surface of the body portion 41 on the tip side. An engaging portion 41c that engages the rotor 10a of the sheath 10 is formed in a tip of the body portion 41. As the rotor 10a engages the engaging portion 41c, the operation unit 40 can be rotated around an axis C1 with respect to the sheath 10.

The sliding portion 42 is provided with a first sliding-side finger-hooking portion (sliding-side finger-hooking portion) 47 and a second sliding-side finger-hooking portion 48 that are arranged side and side in the direction orthogonal to the axis C1 in a side view. A first sliding-side through-hole 47a that penetrates in the orthogonal direction D is formed in the first sliding-side finger-hooking portion 47. A second sliding-side through-hole (through-hole) 48a that penetrates in the orthogonal direction D is formed in the second sliding-side finger-hooking portion 48. The finger-hooking portions 47 and 48 are symmetrical across the axis C1, and are arranged further toward the tip side than the body-side finger-hooking portion 46 in the direction of the axis C1. The through-holes 47a and 48a are formed with sizes such that operator's index finger and middle finger are insertable therethrough.

A connecting connector portion 49 is provided so as to protrude from the second sliding-side finger-hooking portion 48 side in the sliding portion 42. A proximal end portion of the operating wire 20 is fixed to the connecting connector portion 49. This allows the knife unit 30 to be electrically connected to the connecting connector portion 49 via the stopper receiving portion 33 and the operating wire 20. A cord that leads to a high-frequency generator (not shown) is electrically connected to the connecting connector portion 49.

The sliding portion 42 is attached to the body portion 41 so as to be movable in the direction of the axis C1 along the guide groove 41a of the body portion 41.

The regulating portion 43 has a dial portion 52 provided further toward the tip side than the first sliding-side finger-hooking portion 47 in the sliding portion 42, and a movable body (shaft-shaped member) 53 to be screwed to the dial portion 52.

The dial portion 52 is formed in the shape of a disk in a plan view, and is rotatably supported around an axis C2 orthogonal to the axis C1 of the sheath 10 within the accommodating portion 42a formed on the planar portion 41b side in the sliding portion 42. A through-hole (hole) 52a that penetrates in the direction (the thickness direction) of the axis C2 of the dial portion 52 is formed in the dial portion 52. A female thread 52b is formed in an inner peripheral surface of the through-hole 52a. In the present embodiment, as a step portion 52c formed at a bottom surface of the dial portion 52 engages a protrusion 42b provided on a bottom surface of the accommodating portion 42a, the dial portion 52 is rotatably supported within the accommodating portion 42a.

Figure 3:
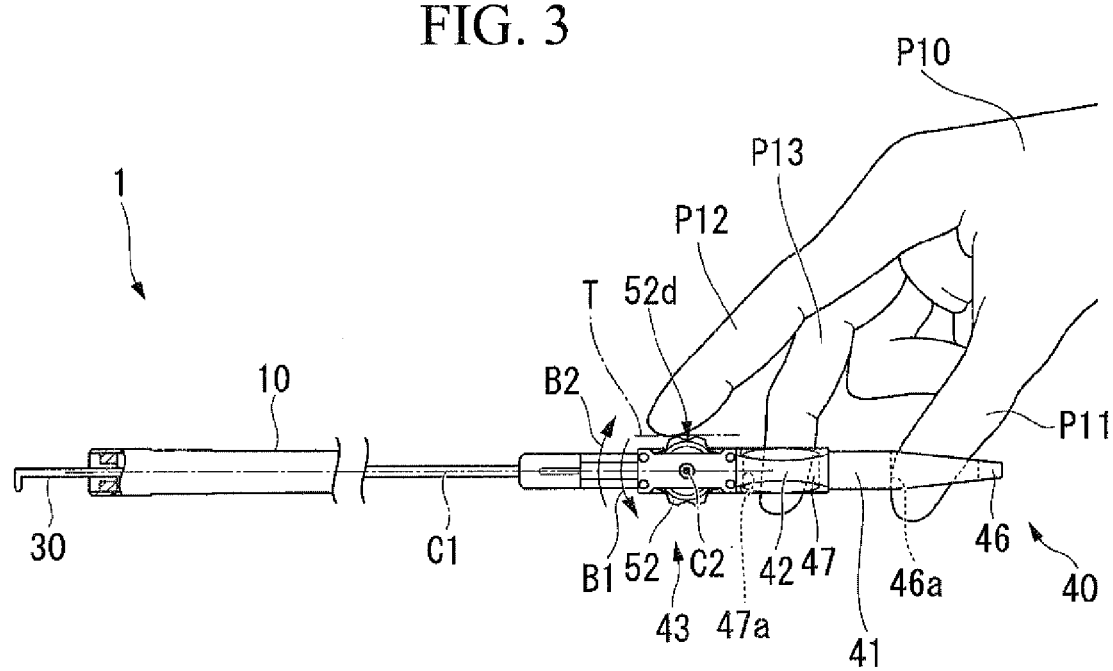
FIG. 3 is a plan view showing a state where an operation unit of the high-frequency knife is gripped.

A portion 52d, which is the edge of the dial portion 52 of which a tangential line T becomes parallel to the axis C1, is exposed to the outside from the sliding portion 42 (refer to FIGS. 2 and 3).

A male thread 53a to be screwed to the female thread 52b of the dial portion 52 is formed in an outer peripheral surface of the movable body 53. In addition, the female thread 52b and the male thread 53a are formed as so-called left-handed threads of which the orientation of helixes are left-handed.

The movable body 53 is arranged on the axis C2. The end portion of the movable body 53 opposite to the body portion 41 is inserted through and supported by a communication hole formed in the sliding portion 42. The end portion of the movable body 53 on the body portion 41 side is provided with a pressing member (elastic member) 54 formed from a material elasticity, such as rubber. The pressing member 54 is formed, for example, in a columnar shape. The pressing member 54 is arranged so that its own bottom surface faces the planar portion 41b of the body portion 41 within a communication hole 42c formed in the bottom surface of the accommodating portion 42a.

As the regulating portion 43 configured in this way turns the dial portion 52 around the axis C2, the movable body 53 is brought close to and separated from the planar portion 41b of the body portion 41 by the screwing between the female thread 52b and the male thread 53a.

In FIGS. 1 and 2, the planar portion 41b of the body portion 41 and the pressing member 54 are separated from each other and the sliding portion 42 is movable in the direction of the axis C1 with respect to the body portion 41.

The high-frequency knife 1 configured in this way is a so-called flexible treatment tool in which the sheath 10 and the operating wire 20 are bendable.

When an operator grips the operation unit 40, in order to effectively transmit the forces of fingertips to the body portion 41 and the sliding portion 42, usually, as shown in FIG. 3, a thumb P11 of a right hand P10 is inserted through the body-side through-hole 46a of the body-side finger-hooking portion 46, an index finger P12 is inserted through the first sliding-side through-hole 47a of the first sliding-side finger-hooking portion 47, and the middle finger P13 is inserted through the second sliding-side through-hole 48a of the second sliding-side finger-hooking portion 48.

Figure 4:
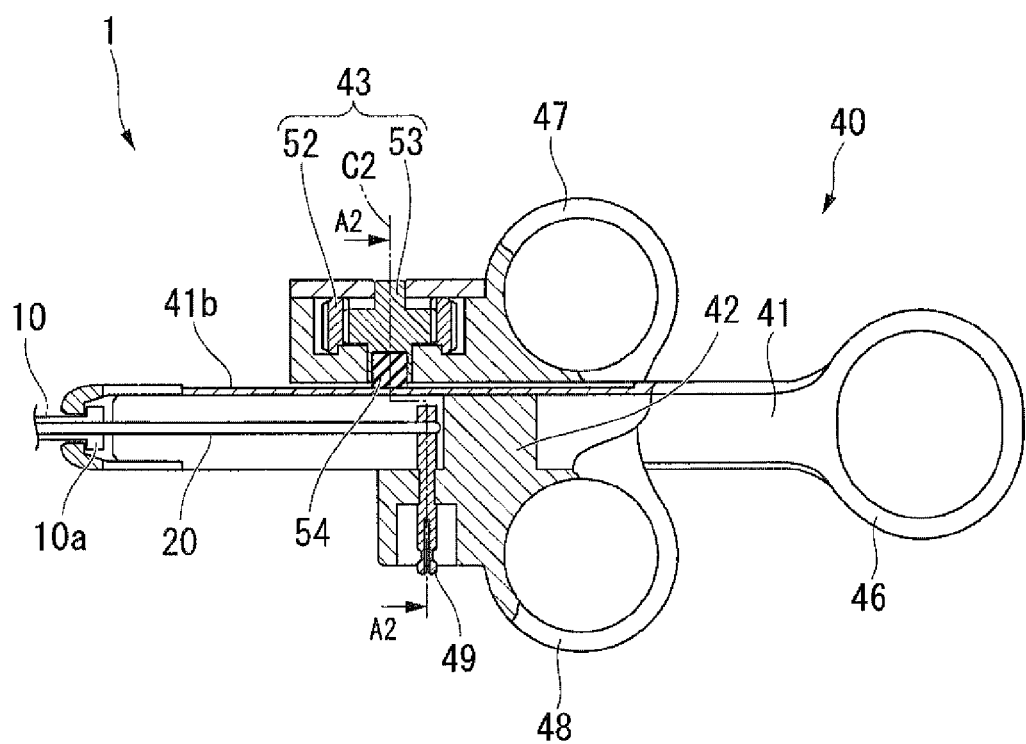
FIG. 4 is a cross-sectional view of a side surface on a base end side when the high-frequency knife is brought into a limited state.
Figure 5:
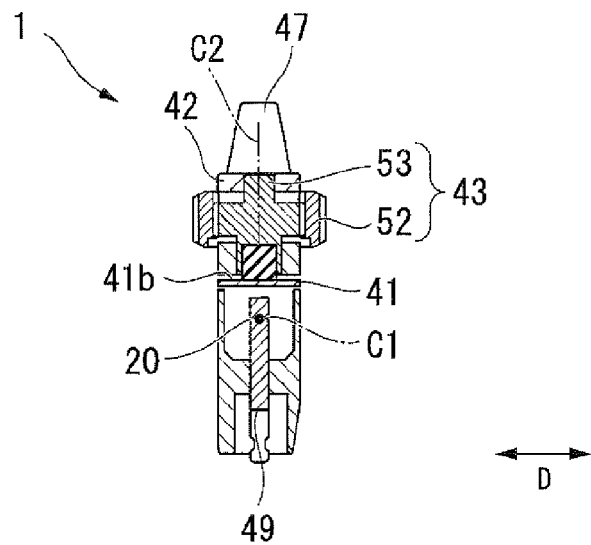
FIG. 5 is a cross-sectional view of cutting line A2-A2 in FIG. 4.

Then, when the dial portion 52 is operated, the index finger P12 is moved forward to move the portion 52d of the dial portion 52 to the tip side in a state where the index finger P12 is taken out of the first sliding-side through-hole 47a and the position of the thumb P11 the position of the middle finger P13 are fixed. This turns the dial portion 52 as shown by arrow B1 around an axis C2. Then, as shown in FIGS. 4 and 5, the movable body 53 moves so as to approach the planar portion 41b of the body portion 41, and presses the pressing member 54 against the planar portion 41b. Since the planar portion 41b is formed in a flat shape, the planar portion 41b and the pressing member 54 are brought into close contact with each other. Accordingly, the body portion 41 is not able to move in the direction of the axis C1 with respect to the pressing member 54, and is brought into a limited state where the movement of the sliding portion 42 in the direction of the axis C1 with respect to the body portion 41 is limited.

The portion 52d of the dial portion 52 are moved to the base end side by the index finger P12 to turn the dial portion 52 as indicated by arrow B2 with a direction opposite to the direction of arrow B1. Accordingly, the movable body 53 is separated from the planar portion 41b, and the regulating portion 43 is brought into a movable state.

In this way, by moving the portion 52d of the dial portion 52 to the tip side or the base end side to turn the dial portion 52 around an axis C2, the regulating portion 43 can be switched between the limited state and the movable state.

Additionally, when the regulating portion 43 is in the movable state, the sliding portion 42 is moved to (pushed into) the tip side in the direction of the axis C1 with respect to the body portion 41 as shown in FIG. 1 by separating the index finger P12 reinserted into the first sliding-side through-hole 47a and separating the middle finger P13 from the thumb P11. Accordingly, the operating wire 20 moves to the tip side with respect to the sheath 10, the stopper receiving portion 33 abuts against the stopper member 11, and the knife unit 30 is positioned in a state where the knife unit 30 protrudes forward from the distal end portion of the sheath 10. The rotation of the knife unit 30 around the axis C1 with respect to the sheath 10 is limited by the contact pressure generated when the stopper receiving portion 33 abuts against the stopper member 11.

Figure 6:
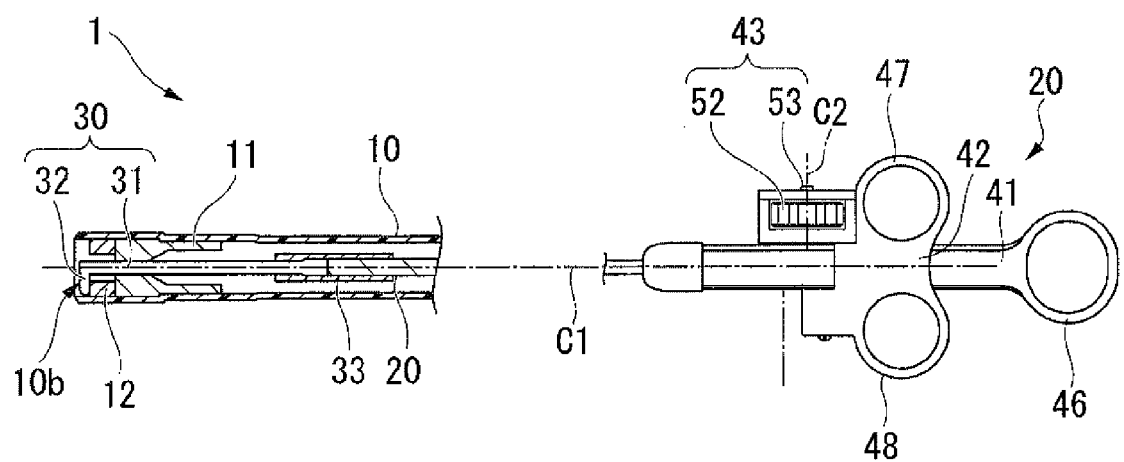
FIG. 6 is a partially cutaway side view when the high-frequency knife is brought into a pull-back state.

On the other hand, if the sliding portion 42 is moved to (pulled back to) the base end side in the direction of the axis C1 with respect to the body portion 41 as shown in FIG. 6 by bringing the index finger P12 and the middle finger P13 close to the thumb P11, the bent portion 32 of the knife unit 30 abuts against a tip surface of the sheath-tip insulating tip 12. At this time, the bent portion 32 of the knife unit 30 is accommodated in the accommodating portion 10b of the sheath 10, and the knife unit 30 is positioned in the pull-back state in which the knife unit 30 is accommodated within the sheath 10.

Next, the operation of the high-frequency knife 1 configured as mentioned above will be described. In the following, for example, the operation when excision of a mucous membrane within a body cavity is endoscopically performed using the high-frequency knife 1 will be described.

Figure 7:
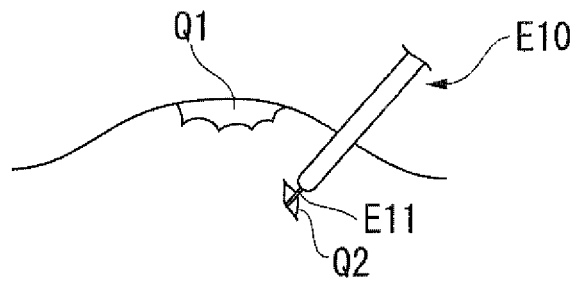
FIG. 7 is a view illustrating a procedure using the high-frequency knife, and is a view showing a state when a hole is made in a portion of a mucous membrane.

First, an injection needle (not shown) is introduced into the body cavity through an endoscope (not shown). Then, as shown in FIG. 7, a physiological salt solution is injected into a submucosal layer of a lesioned mucous membrane portion Q1 that is a target part of the body cavity to be excised, and the lesioned mucous membrane portion Q1 is caused to bulge.

Subsequently, the initial incision of endoscopically introducing a well-known high-frequency knife E10 having a rod-shaped electrode E11 provided at a tip thereof to make a hole Q2 in a portion of the mucous membrane around the lesioned mucous membrane portion Q1 is performed.

Figure 8:
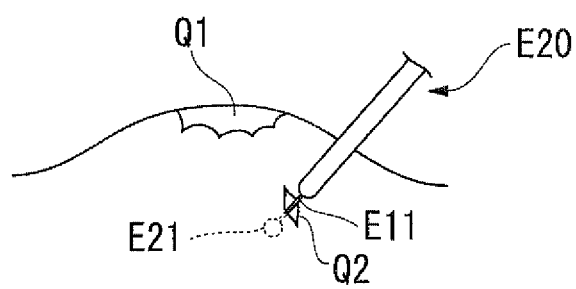
FIG. 8 is a view illustrating the procedure using the high-frequency knife, and is a view showing a state where a larger-diameter portion is inserted into the hole of the mucous membrane.
Figure 9:
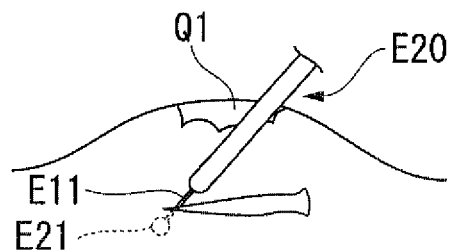
FIG. 9 is a view illustrating the procedure using the high-frequency knife, and is a view showing a state where the high-frequency knife is moved in a transverse direction to perform incision.

Subsequently, as shown in FIG. 8, a well-known high-frequency knife E20 in which a larger-diameter portion E21 formed from an insulating material is provided at a distal end portion of the electrode E11 is similarly introduced into the body cavity via a channel of the endoscope. Then, the larger-diameter portion E21 of the high-frequency knife E20 is inserted into the hole Q2 formed by the initial incision. In this state, while a high-frequency current is applied to an electrode E11, as shown in FIG. 9, the high-frequency knife E20 is moved to incise the periphery of the lesioned mucous membrane portion Q1.

Figure 10:
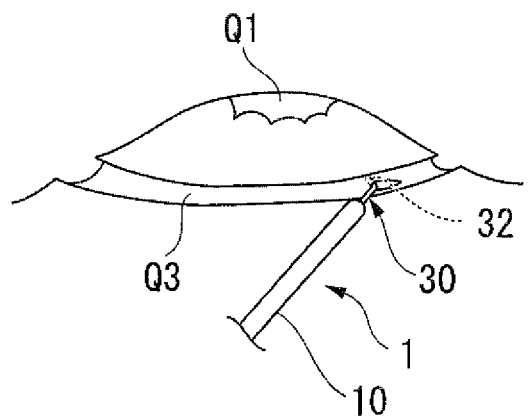
FIG. 10 is a perspective view illustrating the procedure using the high-frequency knife, and illustrating the operation of adjusting the orientation of a bent portion of a knife unit.

Then, after the entire circumference of the lesioned mucous membrane portion Q1 is incised, the high-frequency knife 1 of the present embodiment is used. At this time, the high-frequency knife 1 is brought into the pull-back state where the knife unit 30 is accommodated within the sheath 10 in advance, and the regulating portion 43 is brought into the movable state. In this state, the operator grips the operation unit 40 with the right hand P10 as mentioned above, and introduces the high-frequency knife 1 into the body cavity via the channel of the endoscope. Then, as shown in FIG. 10, the knife unit 30 is made to abut against an opening Q3 formed by incising the periphery of the lesioned mucous membrane portion Q1, the bent portion 32 is hooked, and the submucosal layer of the lesioned mucous membrane portion Q1 is dissected. At this time, it is desirable that the bent portion 32 of the knife unit 30 be parallel to an intrinsic muscle layer or be directed to an inner cavity side.

Figure 11:
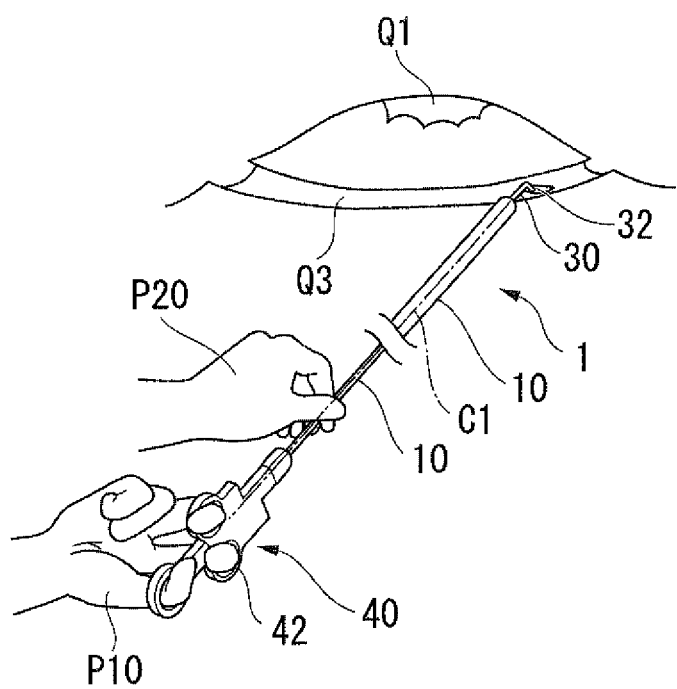
FIG. 11 is a perspective view illustrating the procedure using the high-frequency knife, and illustrating the operation of hooking the bent portion of the knife unit to an opening obtained by incising the periphery of a lesioned mucous membrane portion, and dissecting a submucosal layer of the lesioned mucous membrane portion.

Additionally, when the bent portion 32 is not directed to desirable orientation, the orientation of the bent portion 32 is adjusted by a method as shown in FIG. 11. Specifically, the sheath 10 is gripped with the left hand P20 and the operation unit 40 is rotated, in a state where the sliding portion 42 is slightly pulled back. Subsequently, the sliding portion 42 is pushed and brought into the push state by pushing out the index finger P12 and the middle finger P13 inserted through the through-holes 47a and 48a forward with respect to the thumb P11 of the right hand P10 inserted through the body-side through-hole 46a after the orientation of the bent portion 32 is changed. The rotation of the knife unit 30 around the axis C1 is limited by the contact pressure generated when the stopper receiving portion 33 abuts against the stopper member 11.

As shown in FIG. 3, the index finger P12 is taken out of the first sliding-side through-hole 47a in a state where the middle finger P13 is pushed out forward with respect to the thumb P11. By moving the index finger P12 forward to move the portion 52d of the dial portion 52 to the tip side, the dial portion 52 is turned as shown by arrow B1. Accordingly, as shown in FIGS. 4 and 5, the pressing member 54 abuts against the planar portion 41b, and the regulating portion 43 is brought into the limited state.

Accordingly, the knife unit 30 is fixed to the sheath 10 and also the endoscope in a state where the bent portion 32 maintains desired orientation. Since the orientation of the bent portion 32 is fixed, mucous membrane incision can be safely performed.

A high-frequency current is supplied to the knife unit 30 by connecting the cord of the high-frequency generator to the connecting connector portion 49, and the incision (treatment) of the submucosal layer of the lesioned mucous membrane portion Q1 is continued.

Then, after all the lesioned mucous membrane portion Q1 is excised, the lesioned mucous membrane portion Q1 is gripped by gripping forceps (not shown), is endoscopically taken out to the outside of a patient's body, and the treatment is ended.

As described above, according to the high-frequency knife 1 of the present embodiment, the regulating portion 43 is switched to the movable state by moving the portion 52d of the dial portion 52 to the base end side in the direction of the axis C1 with the index finger P12 when being in the limited state when the movement of the sliding portion 42 in the direction of the axis C1 with respect to the body portion 41 is limited. Similarly, the regulating portion 43 is switched to the limited state by moving the portion 52d of the dial portion 52 to the tip side in the direction of the axis C1 with the index finger P12 when the regulating portion 43 is in the movable state.

Since the direction of the axis C1 in which the sliding portion 42 is moved with respect to the body portion 41, and the direction in which the portion 52d of the dial portion 52 when switching is performed between the movable state and the limited state is moved are parallel to each other, the operation caused by the index finger P12 that switches the regulating portion 43 between the movable state and the limited state can be easily performed.

Both the orientation in which the middle finger P13 is pushed out when the stopper receiving portion 33 is pressed against the stopper member 11 and the orientation in which the portion 52d of the dial portion 52 is moved when the regulating portion 43 is switched from the movable state to the limited state are the same as the front. Accordingly, the index finger P12 is easily powered during the operation of the dial portion 52, and the operation of the dial portion 52 by the index finger P12 can be easily performed.

Since the portion 52d of the dial portion 52 of the regulating portion 43 is exposed to the outside, the portion 52d can be easily operated with the index finger P12.

The regulating portion 43 has the dial portion 52 and the movable body 53. Accordingly, a mechanism in which the movable body 53 is brought close to and separated from the planar portion 41b by turning the dial portion 52 can be easily and cheaply configured.

The planar portion 41b is formed in the body portion 41. For this reason, the body portion 41 and the pressing member 54 can be brought into close contact with each other, and the movement of the sliding portion 42 in the direction of the axis C1 with respect to the body portion 41 can be reliably limited.

The end portion of the movable body 53 on the body portion 41 side is provided with the pressing member 54. Accordingly, the body portion 41 and the movable body 53 can be reliably brought into contact with each other via the pressing member 54, and the movement of the sliding portion 42 can be more reliably limited.

In the present embodiment, the turning angle of the dial portion 52 required when switching is performed between the movable state and the limited state can be made small by making the gap between the planar portion 41b of the body portion 41 and the pressing member 54 in the movable state small or by enlarging the pitch of the female thread 52b of the dial portion 52 and the male thread 53a of the movable body 53.

Figure 12:
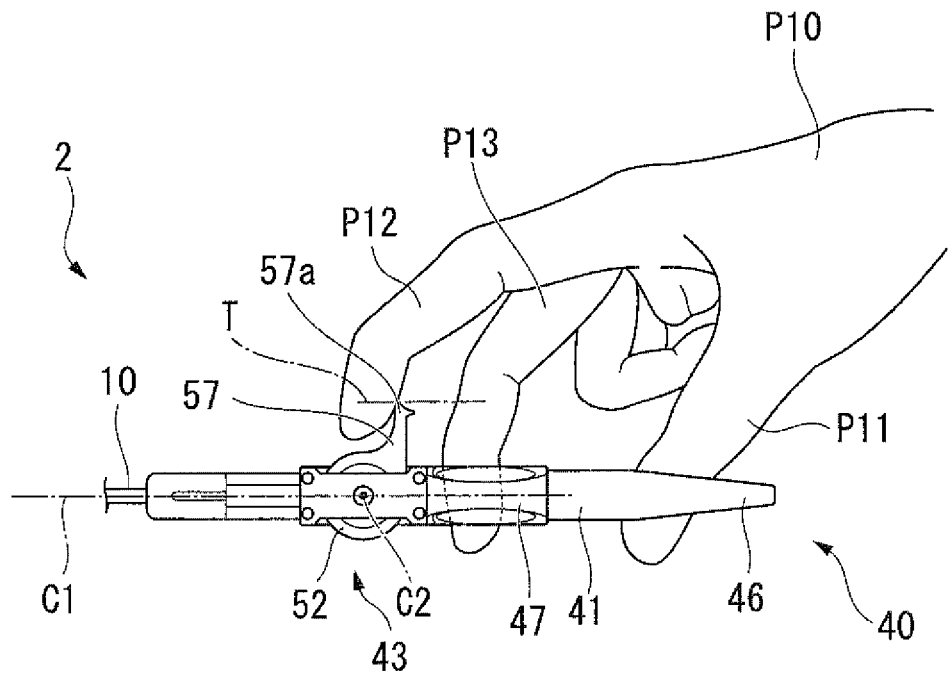
FIG. 12 is a plan view on the base end side when a high-frequency knife in a modification example of the first embodiment of the present invention is brought into a movable state.

For example, in a high-frequency knife 2 of the modification example of the present embodiment shown in FIG. 12, the dial portion 52 is provided with a knob 57 that protrudes radially outward. In this case, a portion 57a of the knob 57 serving as a distal end portion in a protruding direction is an edge of the dial portion 52, and a tangential line T of this edge is a portion that is parallel to the axis C1.

Figure 13:
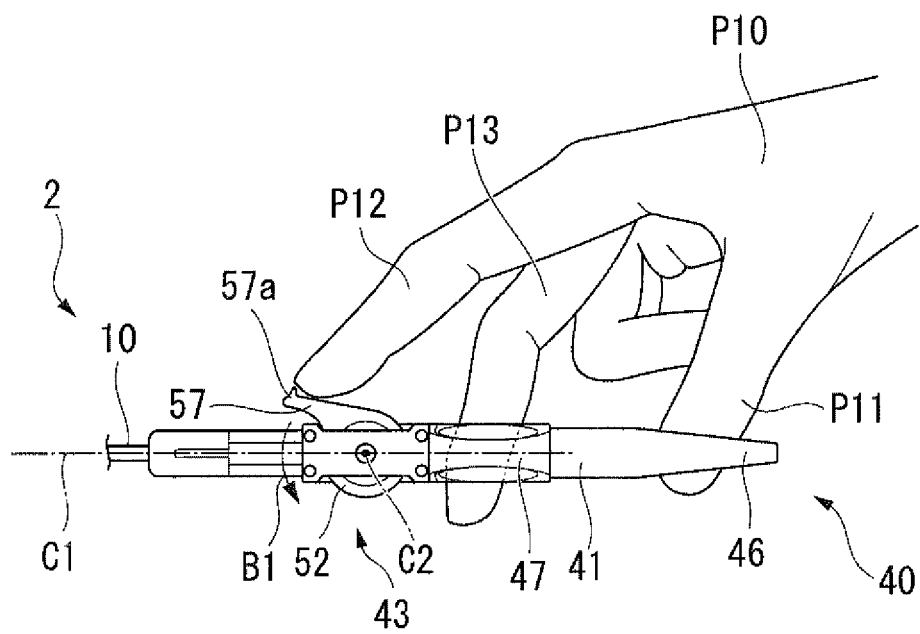
FIG. 13 is a plan view on the base end side when the high-frequency knife is brought into a limited state.

The index finger P12 is hooked to the portion 57a of the knob 57 when the regulating portion 43 shown in FIG. 12 is in the movable state. By moving the index finger P12 to the tip side as shown in FIG. 13, the dial portion 52 is turned around the axis C2 as shown by arrow B1. In this example, switching is performed from the movable state to the limited state by turning the dial portion 52 by about 90 degrees around the axis C2.

In the high-frequency knife 2 of the modification example configured in this way, the turning angle of the dial portion 52 required when switching is performed between the movable state and the limited state can be made small to such a degree that operation is not hindered. Additionally, by providing the dial portion 52 with the knob 57, a force required to turn the dial portion 52 can be reduced.

In the present embodiment, when a frictional force generated when the movable body 53 is pressed against the body portion 41 is relatively great, the planar portion 41b may not be formed at the body portion 41. Additionally, the pressing member 54 may not be provided at the movable body 53.

Although the dial portion 52 is formed in the shape of a disk in a plan view, the shape of the dial portion 52 is not limited to this. For example, by discretely forming a slip-preventing groove portion in a circumferential direction at the edge of the dial portion, the dial portion may be formed in a polygonal shape, such as a hexagonal shape, in the shape of a star, or the like in a plan view.

In the present embodiment, the through-hole 52a is formed in the dial portion 52, the female thread 52b is formed in the inner peripheral surface of the through-hole 52a, and the male thread 53a to be screwed to the female thread 52b of the dial portion 52 is formed in the outer peripheral surface of the movable body 53. However, the through-hole may be formed in the axis direction of the movable body, the female thread is formed in the inner peripheral surface of the through hole, and the male thread to be screwed to the female thread of the movable body may be formed in the outer peripheral surface of the dial portion.

Even if the present invention is configured in this way, the same effects as the present embodiment can be exhibited.

Second Embodiment

Next, although a second embodiment of the present invention will be described referring to FIGS. 14 to 17, the same parts as the above embodiment will be designated by the same reference numerals and the description thereof will be omitted, and only different points will be described.

Figure 14:
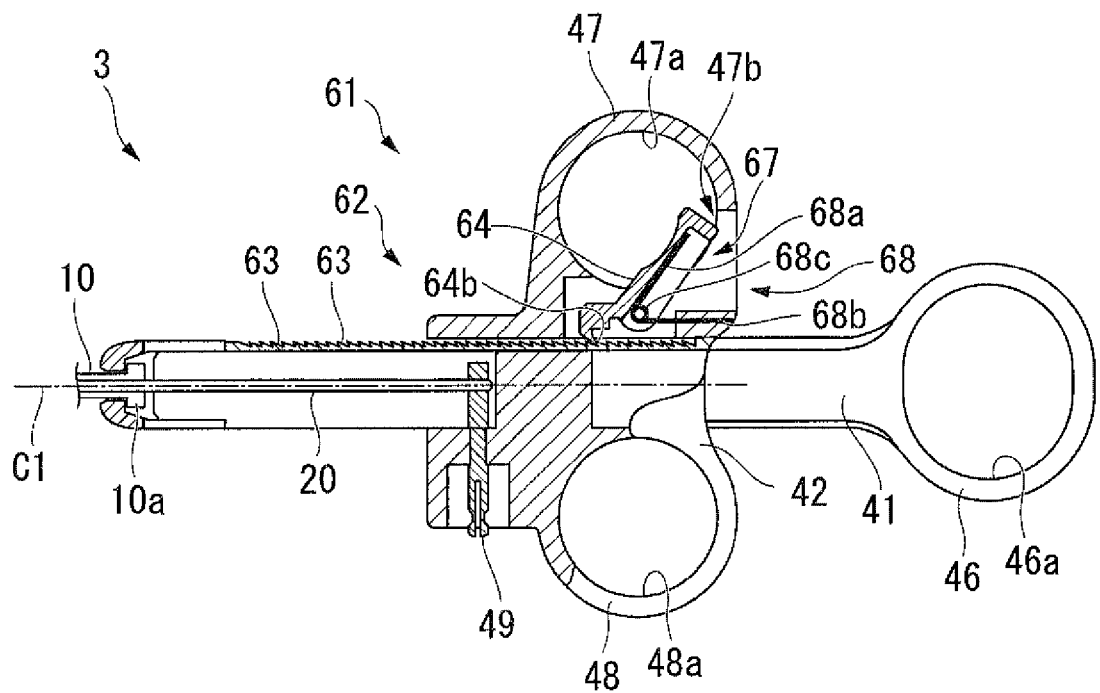
FIG. 14 is a cross-sectional view of a side surface on a base end side when a high-frequency knife of a second embodiment of the present invention is brought into a limited state.

As shown in FIG. 14, a high-frequency knife 3 of the present embodiment includes a regulating portion 61 having a ratchet portion 62, instead of the regulating portion 43 in the high-frequency knife 1 of the first embodiment.

The ratchet portion 62 has a plurality of body-side claw portions 63 provided instead of the planar portion 41b in the body portion 41, and a sliding-side claw portion 64 that are rotatably supported by the sliding portion 42.

The plurality of body-side claw portions 63 are arranged side by side along the axis C1 on a side surface of the body portion 41. The respective body-side claw portions 63 are formed in a substantially triangular shape in a side view. The body-side claw portions 63 are formed so that the surfaces thereof on the tip side are orthogonal to the axis C1 and so that the surfaces thereof on the base end side approach the axis C1 towards the base end side.

An accommodating portion 67 is formed in a portion between the first sliding-side finger-hooking portion 47 in the sliding portion 42 and the axis C1. The accommodating portion 67 communicates with an opening 47b formed in the inner peripheral surface of the first sliding-side through-hole 47a on the base end side, and an opening 42d formed in the sliding portion 42 so as to face the body-side claw portions 63, respectively.

The sliding-side claw portion 64 is fixed to one arm portion 68a of a torsion spring 68 in a state where the portion thereof is disposed within the accommodating portion 67. Another arm portion 68b of the torsion spring 68 is fixed to the sliding portion 42. A button (a portion of the regulating portion 61) 64a is provided near the distal end portion of sliding-side claw portion 64 in an extending direction in which one arm portion 68a extends. The button 64a is provided in a state where the button is exposed to the base end side within the first sliding-side through-hole 47a. The end portion of the sliding-side claw portion 64 opposite to the button 64a is provided with a claw 64b engageable with the body-side claw portions 63.

In the high-frequency knife 3 configured in this way, the body-side claw portions 63 are engaged with the claw 64b as the arm portion 68a is turned around a connecting portion 68c between the arm portion 68a and the arm portion 68b by the biasing force of the torsion spring 68. At this time, a state where the movement (pull-back) of the sliding portion 42 to the base end side with respect to the body portion 41 is limited by the engagement between body-side claw portions 63 and the claw 64b is a limited state. It should be noted that, even in this limited state, the sliding portion 42 can be moved (pushed) to the tip side with respect to the body portion 41.

Figure 15:
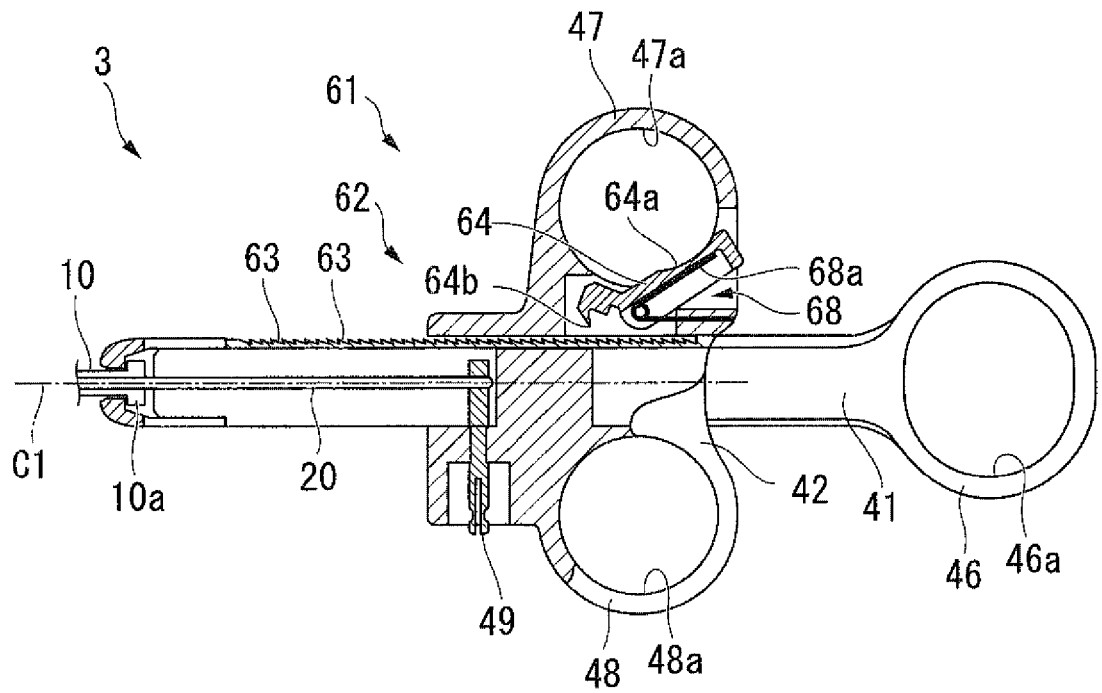
FIG. 15 is a cross-sectional view of the side surface on the base end side when the high-frequency knife is brought into a movable state.

Meanwhile, if the operator inserts the index finger P12 or the like into the first sliding-side through-hole 47a and moves the button 64a on the base end side as shown in FIG. 15 with the inserted index finger P12, the sliding-side claw portion 64 is turned around the connecting portion 68c, and the engagement between the body-side claw portions 63 and the claw 64b is released. Accordingly, the sliding portion 42 can be switched to the movable state where the sliding portion is movable both to the tip side and to the base end side with respect to the body portion 41.

Figure 16:
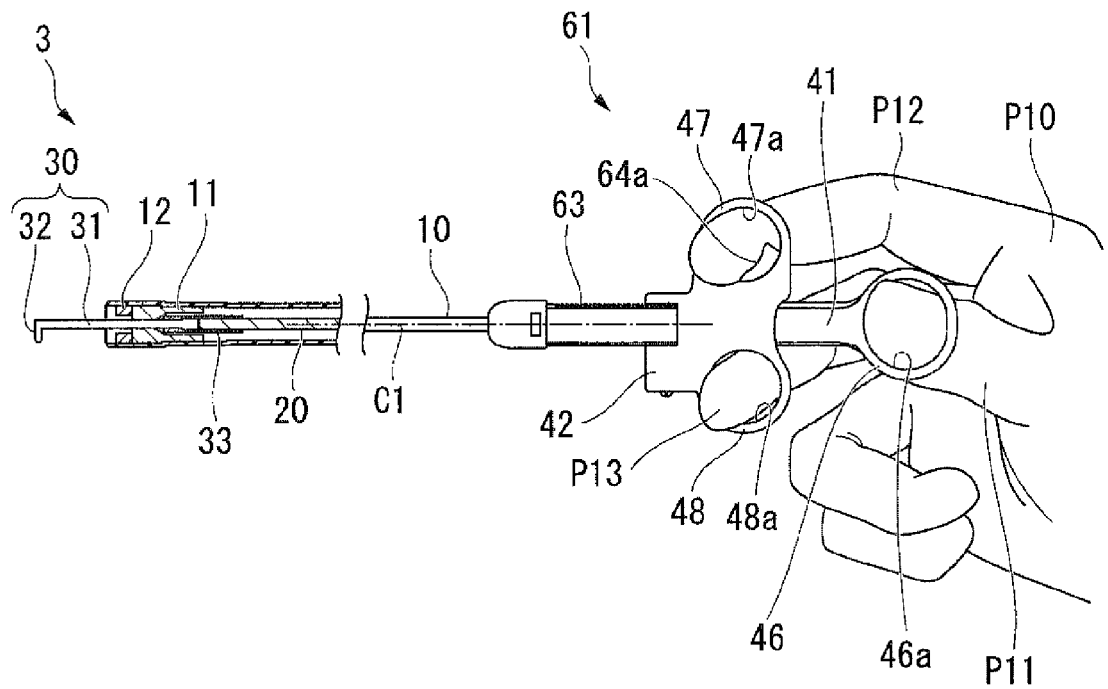
FIG. 16 is a partially cutaway side view when the high-frequency knife is brought into a push state.

When mucous membrane incision within the body cavity is performed using the high-frequency knife 3 configured in this way, as shown in FIG. 16, the sliding portion 42 is pushed and brought into the push state by pushing out the index finger P12 and the middle finger P13 inserted through the through-hole 47a and the through-hole 48a forward with respect to the thumb P11 of the right hand P10 inserted through the body-side through-hole 46a. At this time, since the index finger P12 biases the first sliding-side finger-hooking portion 47 so as to be pushed out forward within the first sliding-side through-hole 47a, the index finger P12 is in a state where the index finger comes in contact with the inner peripheral surface of the first sliding-side through-hole 47a on the tip side and does not come in contact with the button 64a.

The stopper receiving portion 33 abuts against the stopper member 11, the contact pressure acts on the stopper member, and the rotation of the knife unit 30 around an axis C1 with respect to the sheath 10 is limited.

If the forward push-out by the index finger P12 and the middle finger P13 is stopped, the sliding portion 42 is pushed back to the base end side via the stopper receiving portion 33 and the operating wire 20 by the reaction force of the stopper member 11. However, since the regulating portion 61 is in the limited state, the sliding portion 42 is not pulled back to the base end side, and a state where the rotation of the knife unit 30 is limited is maintained.

Figure 17:
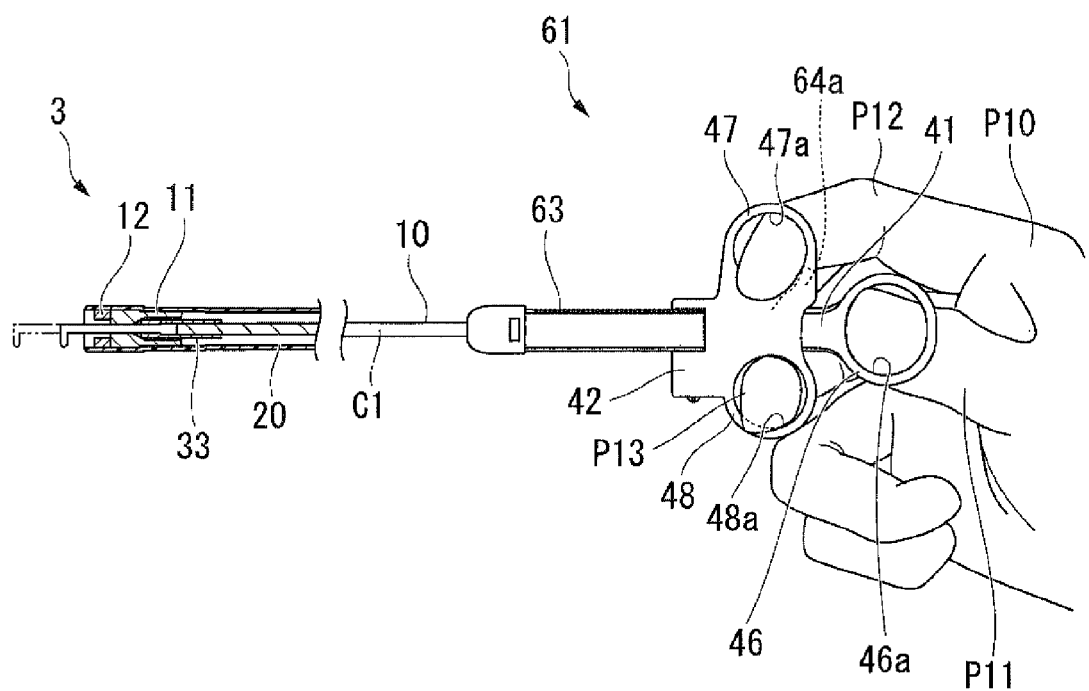
FIG. 17 is a partially cutaway side view when the high-frequency knife is brought into a pull-back state.

When the sliding portion 42 is pulled back and brought into the pulled-back state where the knife unit 30 is accommodated within the sheath 10, as shown in FIG. 17, the index finger P12 inserted through the first sliding-side through-hole 47a is moved to the base end side. Accordingly, the button 64a biased to the index finger P12 moves to the base end side, the engagement between body-side claw portions 63 and the claw 64b are released, and the regulating portion 61 is switched to the movable state. Accordingly, the sliding portion 42 can be pulled back.

As described above, according to the high-frequency knife 3 of the present embodiment, switching is performed from the limited state to the movable state simply by moving the button 64a to the base end side, and if the button 64a is returned to its original position, switching is performed from the movable state to the limited state. For this reason, the switching between the movable state and the limited state can be easily performed.

Third Embodiment

Next, although a third embodiment of the present invention will be described referring to FIGS. 18 to 20, the same parts as the above embodiment will be designated by the same reference numerals and the description thereof will be omitted, and only different points will be described.

Figure 18:
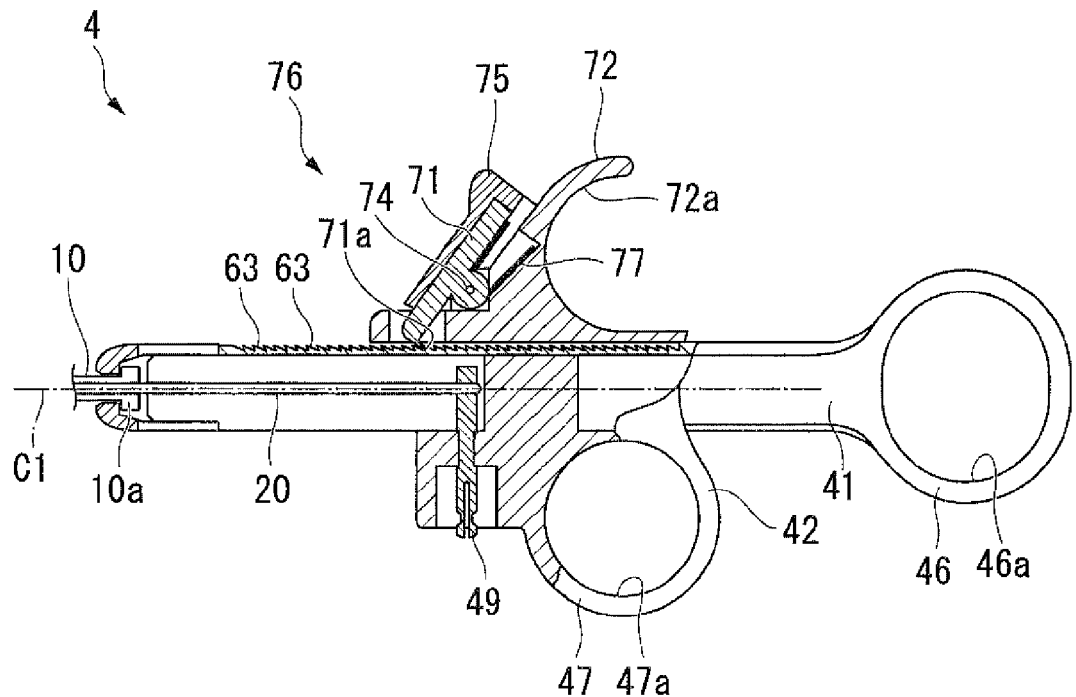
FIG. 18 is a cross-sectional view of a side surface on a base end side when a high-frequency knife of a third embodiment of the present invention is brought into a limited state.

As shown in FIG. 18, a high-frequency knife 4 of the present embodiment includes a sliding-side claw portion 71 instead of the sliding-side claw portion 64 in the high-frequency knife 3 of the second embodiment.

In the present embodiment, the first sliding-side finger-hooking portion 47 is provided on the connecting connector portion 49 side in the sliding portion 42. The second sliding-side finger-hooking portion 72 is provided opposite to the first sliding-side finger-hooking portion 47 with respect to the axis C1 in the sliding portion 42. In this example, a finger-hooking recess 72a formed in a shape that is recessed toward the tip side in a side view is formed in the second sliding-side finger-hooking portion 72.

An intermediate portion of the aforementioned sliding-side claw portion 71 in the longitudinal direction is rotatably supported by a pin 74 provided on the sliding portion 42 further toward the tip side than the second sliding-side finger-hooking portion 72. A distal end portion of the sliding-side claw portion 71 is provided with a claw 71a that is engageable with the body-side claw portions 63 formed at the body portion 41. A torsion spring 77 is attached between the sliding-side claw portion 71 and the sliding portion 42, and the torsion spring 77 is biased so that the claw 71a engages the body-side claw portions 63. A cover 75 formed from a material having elasticity, such as rubber, is attached to the portion of the sliding-side claw portion 71 from an intermediate portion to a proximal end portion.

In addition, the plurality of body-side claw portions 63 and the sliding-side claw portion 71 constitute the regulating portion 76.

The high-frequency knife 4 configured in this way is brought into the limited state where the claw 71a is engaged with the body-side claw portions 63 similar to the second embodiment and the pull-back of the sliding portion 42 with respect to the body portion 41 is limited, in a state where the operator does not operate the sliding-side claw portion 71. It should be noted that, even in this limited state, the sliding portion 42 can be pushed and brought into the push state by pushing out the index finger P12 pressed against the finger-hooking recess 72a and the middle finger P13 inserted through the first sliding-side through-hole 47a forward with respect to the thumb P11 inserted through the body-side through-hole 46a.

Figure 19:
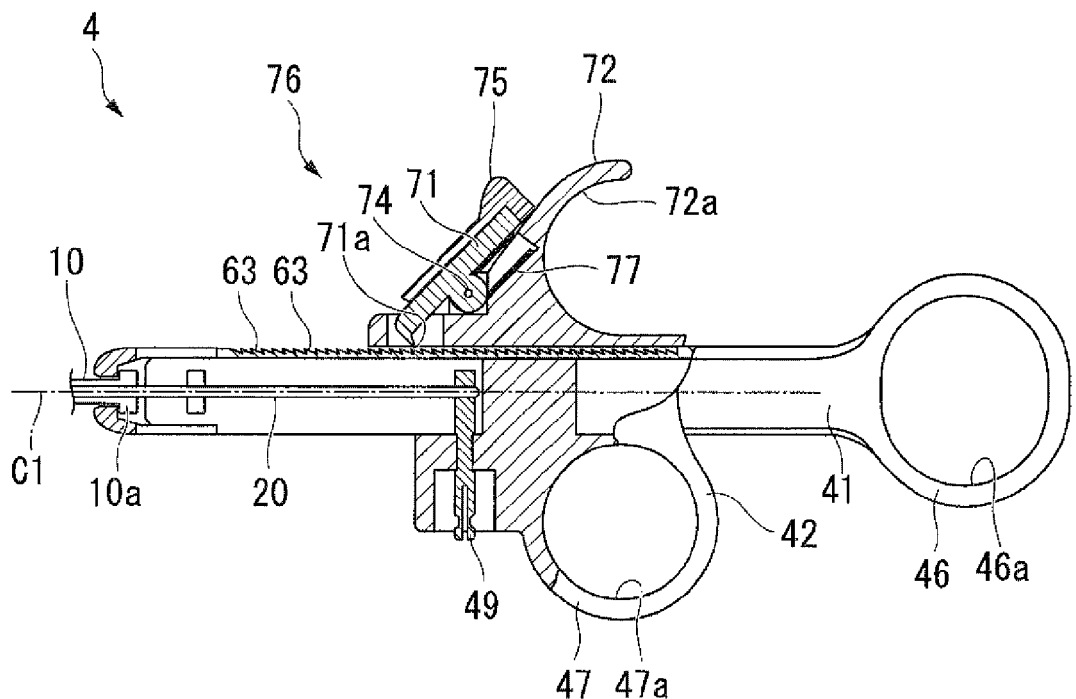
FIG. 19 is a cross-sectional view of the side surface on the base end side when the high-frequency knife is brought into a movable state.
Figure 20:
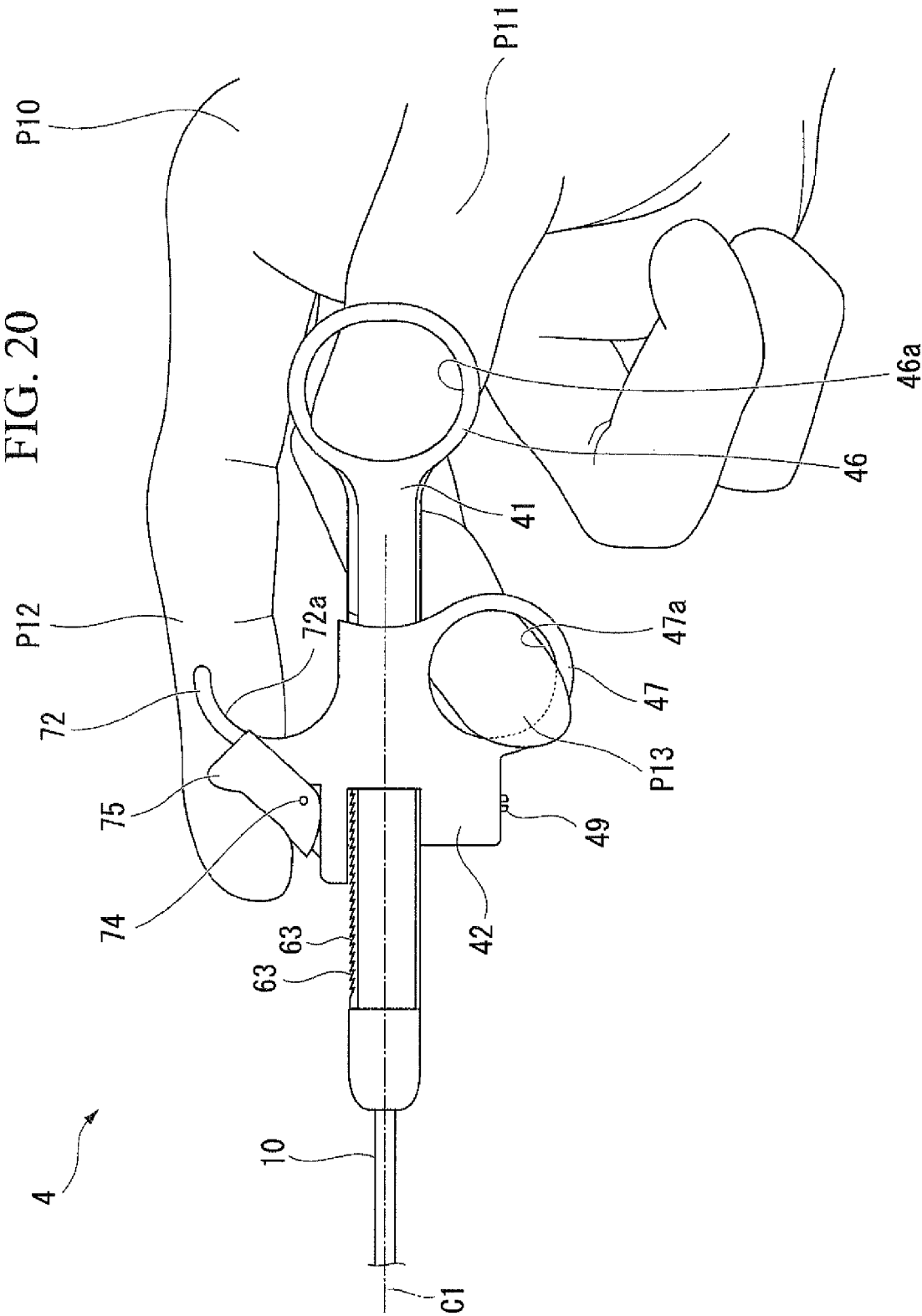
FIG. 20 is a side view on the base end side when the high-frequency knife is brought into the movable state.

On the other hand, when the sliding portion 42 is pulled back, as shown in FIGS. 19 and 20, the index finger P12 is separated from the finger-hooking recess 72a, the proximal end portion of the cover 75 is moved to the base end side with the index finger P12, and the engagement between the body-side claw portions 63 and the claw 71a is released against the biasing force of the torsion spring 77.

As described above, according to the high-frequency knife 4 of the present embodiment, the switching between the movable state and the limited state can be easily performed.

Additionally, by providing the sliding-side claw portion 71 in a place apart from the finger-hooking recess 72a that presses the index finger P12 when the sliding portion 42 is pushed, the sliding-side claw portion 71 can be kept from being unintentionally operated.

Fourth Embodiment

Next, although a fourth embodiment of the present invention will be described referring to FIGS. 21 and 22, the same parts as the above embodiment will be designated by the same reference numerals and the description thereof will be omitted, and only different points will be described. In the present embodiment, a case where the medical treatment instrument is a grip operating device will be described.

Figure 21:
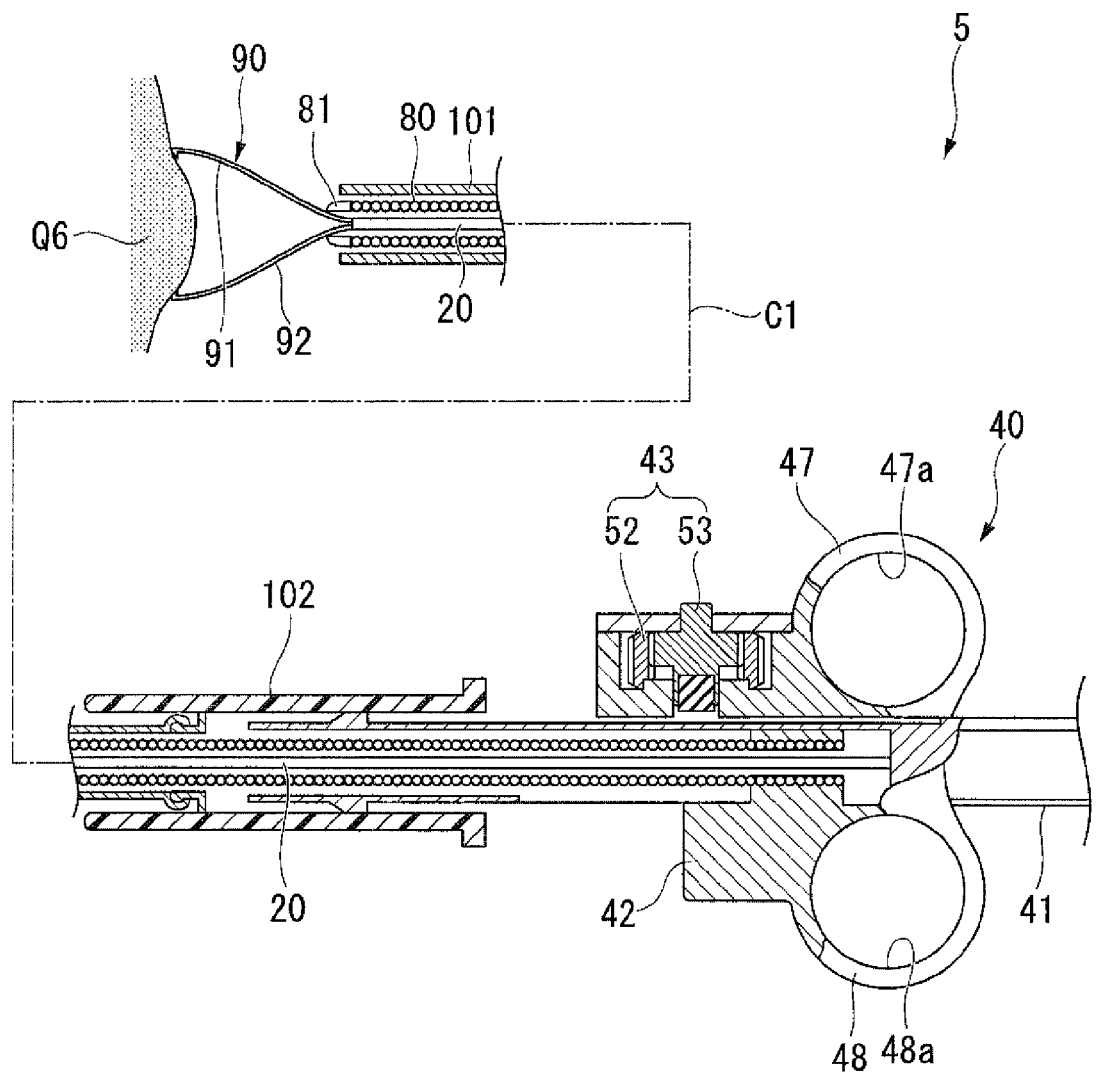
FIG. 21 is a cross-sectional view of a side surface when a high-frequency knife of a fourth embodiment of the present invention is brought into a pull-back state and a movable state.
Figure 22:
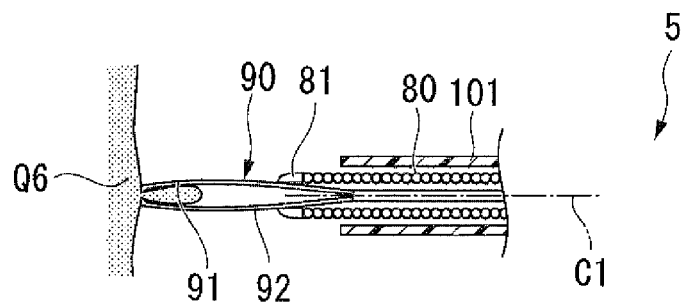
FIG. 22 is a cross-sectional view of the side surface on a tip side when the high-frequency knife is brought into a push state.

As shown in FIG. 21, the grip operating device 5 of the present embodiment includes a sheath 80 having flexibility, the operating wire 20 retractably inserted through the sheath 80, forceps (treatment unit) 90 provided at the distal end portion of the operating wire 20, and the aforementioned operation unit 40 provided at a proximal end portion of the sheath 80.

In the present embodiment, the sheath 80 is formed from, for example, a closely wound coil.

A hollow tubular body 81 is attached to a distal end portion of the sheath 80. The forceps 90 has a pair of forceps pieces 91 and 92, proximal end portions of the forceps pieces 91 and 92 are fixed to the distal end portion of the operating wire 20, and distal end portions of the forceps pieces 91 and 92 are configured so as to be separated for each other in a natural state where an external force does not act.

The proximal end portion of the operating wire 20 is fixed to the body portion 41. Meanwhile, the proximal end portion of the sheath 80 is fixed to the sliding portion 42.

The sheath 80 is inserted through a sheathing tube 101. A proximal end portion of the sheathing tube 101 is attached to a body outer tube 102 disposed so as to surround that the body portion 41.

In the grip operating device 5 configured in this way, the tubular body 81 is arranged further toward the base end side than the forceps 90 in the pull-back state where the sliding portion 42 is pulled back shown in FIG. 21, and thus, the forceps pieces 91 and 92 are brought into an open state. A tissue Q6 is pressed between the forceps pieces 91 and 92 in the open state, and fingers are hooked to the finger-hooking portions 46, 47, and 48 to push-in the sliding portion 42 and bring the sliding portion into the push state. Then, as shown in FIG. 22, the forceps pieces 91 and 92 are pulled into a tube hole of the tubular body 81 and are closed as the tubular body 81 moves to the tip side with respect to the forceps 90. At this time, the tissue Q6 is pinched and gripped between the forceps pieces 91 and 92.

Generally, in the endoscopic submucosal dissection (ESD), incision is performed using a high-frequency knife or the like in a state where a tissue is gripped by a grip operating device or the like. In the grip operating device 5 of the present embodiment, a state where the forceps pieces 91 and 92 are closed is maintained when the sliding portion 42 is pushed and brought into the push state. Therefore, the forceps pieces 91 and 92 do not open unintentionally.

Although the first to fourth embodiments of the present invention have been described above in detail with reference to the drawings, specific configuration is not limited to the embodiments, and changes of the configuration are also included without departing from the scope of the present invention. Moreover, it is obvious that the respective configurations shown in the respective embodiments may be combined and used appropriately.

For example, if one finger-hooking portion (first sliding-side finger-hooking portion 47) is formed in the sliding portion 42, it is possible to hook a finger to the finger-hooking portion and move the sliding portion 42. Therefore, in the above first, second, and fourth embodiments, the operation unit may not be provided with the second sliding-side finger-hooking portion 48.

In the first to fourth embodiments, the female thread 52b and the male thread 53a of the operation unit 40 are formed as left-handed threads. However, when a left-handed operator uses the present invention, it is preferable to form the female thread 52b and the male thread 53a as so-called right-handed threads.

Although the sheath is formed from a material having flexibility, the sheath may be formed from a hard material, such as stainless steel. In this case, a high-frequency knife, which is a so-called rigid treatment tool, can be inserted through a channel of a hard mirror in which an insertion section does not bend, and can be used.

The operation unit having the body portion 41, the sliding portion 42, and the regulating portion in the medical treatment instrument of the present invention, is not limited to medical applications, but also can be preferably used for various kinds of experiments and research, as an operation unit for operating a robot, or the like.

Although the preferred examples of the present invention have been described above, the present invention is not limited to these examples. Additions, omissions, substitutions, and other modifications of components can be made without departing from the concept of the present invention. The present invention is not to be considered as being limited by the foregoing description, and is limited only by the scope of the appended claims.

The invention claimed is:

1. A medical treatment instrument comprising:
   a sheath;
   an operating member that is advanced and retracted, and is inserted into the sheath;
   a treatment unit that is provided at a distal end portion of the operating member; and
   an operation unit that has a body portion connected to a proximal end portion of the sheath and that causes the operating member to be advanced and retracted with respect to the sheath and to be rotated around a longitudinal axis of the body portion,
   wherein the operation unit includes:
      a sliding portion that is capable of advancing and retracting with respect to the body portion and rotating around the longitudinal axis of the body portion and that is connected to a proximal end portion of the operating member; and
      a regulating portion that is switchable to a movable state where the sliding portion is capable of advancing, retracting, and rotating with respect to the body portion and a limited state where the advancing, retracting, and rotating of the sliding portion with respect to the body portion is limited,
   wherein the regulating portion includes:
      a dial portion that is rotatable around an axis orthogonal to the longitudinal axis; and a shaft-shaped member that is screwed to the dial portion and that is capable of advancing and retracting relative to the dial portion in a direction in which the shaft-shaped member comes close to and separates from the body portion, and wherein rotation of the dial portion about the axis orthogonal to the longitudinal axis causes the shaft-shaped member to move so that the shaft-shaped member come close to and separates from the body portion.

2. The medical treatment instrument according to claim 1, wherein the body portion has a body-side finger-hooking portion, wherein the sliding portion has a sliding-side finger-hooking portion located further toward a tip side than the body-side finger-hooking portion, and wherein the regulating portion is provided further toward the tip side than the sliding-side finger-hooking portion.

3. The medical treatment instrument according to claim 2, wherein at least a portion of the dial portion is exposed to an outside from an outer peripheral surface of the sliding portion.

4. The medical treatment instrument according to claim 3, wherein a hole that penetrates in a direction of the axis of the dial portion is formed, wherein a female thread is formed in an inner peripheral surface of the hole, and wherein the shaft-shaped member advances and retracts in the direction of the axis with respect to the dial portion in response to the turning of the dial portion by a male thread to be screwed to the female thread being formed in an outer peripheral surface of the shaft-shaped member.

5. The medical treatment instrument according to claim 3, wherein a plane parallel to an advance and retraction direction of the sliding portion for contacting an end portion of the shaft-shaped member is formed on the shaft-shaped member side of the body portion.

6. The medical treatment instrument according to claim 5, where an end portion of a body portion side of the shaft-shaped member is provided with an elastic member that contacts the plane.

7. The medical treatment instrument according to claim 1, wherein upon rotation of the dial portion about the axis orthogonal to the longitudinal axis, the location of the dial portion with respect to the body portion remains constant.

8. The medical treatment instrument according to claim 1, wherein the dial portion does not move toward and away from the body portion.

* * * * *